(12) United States Patent
Lalvani et al.

US008617821B2

(10) Patent No.: US 8,617,821 B2
(45) Date of Patent: *Dec. 31, 2013

(54) ASSAY METHOD FOR PEPTIDE SPECIFIC T-CELLS

(75) Inventors: Ajit Lalvani, Oxford (GB); Roger Hamilton Brookes, Toronto (CA)

(73) Assignee: Isis Innovation Limited, Oxford (GB)

( * ) Notice: Subject to any disclaimer, the term of this patent is extended or adjusted under 35 U.S.C. 154(b) by 513 days.

This patent is subject to a terminal disclaimer.

(21) Appl. No.: 12/510,594

(22) Filed: Jul. 28, 2009

(65) Prior Publication Data

US 2010/0203568 A1 Aug. 12, 2010

Related U.S. Application Data

(63) Continuation of application No. 09/308,725, filed on May 24, 1999, now Pat. No. 7,575,870, which is a continuation of application No. PCT/GB97/03222, filed on Nov. 25, 1997.

(30) Foreign Application Priority Data

Nov. 25, 1996 (GB) .................................. 9624456.1

(51) Int. Cl.
*G01N 33/532* (2006.01)
*A61K 39/04* (2006.01)

(52) U.S. Cl.
USPC ........................................ 435/7.1; 424/248.1

(58) Field of Classification Search
None
See application file for complete search history.

(56) References Cited

U.S. PATENT DOCUMENTS

| | | | |
|---|---|---|---|
| 5,939,281 A | 8/1999 | Lehmann et al. | |
| 5,955,077 A | 9/1999 | Andersen et al. | |
| 6,410,252 B1 | 6/2002 | Lehmann et al. | |
| 7,115,361 B2 | 10/2006 | Lalvani et al. | |
| 7,575,870 B1 * | 8/2009 | Lalvani et al. | 435/7.1 |
| 7,632,646 B1 * | 12/2009 | Lalvani et al. | 435/7.1 |
| 2002/0114816 A1 | 8/2002 | Endl et al. | |
| 2002/0131976 A1 | 9/2002 | Lalvani et al. | |
| 2002/0136733 A1 | 9/2002 | Hill et al. | |
| 2004/0058399 A1 | 3/2004 | Lalvani | |
| 2004/0141985 A1 | 7/2004 | Lalvani et al. | |

FOREIGN PATENT DOCUMENTS

| | | |
|---|---|---|
| DE | 19525784 | 1/1997 |
| EP | 0296158 | 6/1992 |
| WO | WO 95/01441 | 1/1995 |
| WO | WO 97/00067 | 1/1997 |

OTHER PUBLICATIONS

Abbas et al. Cellular and Molecular Immunobiology, Fifth Ed., Saunders, p. 166 (2005).

Ahmed et al. "Immunological memory and protective immunity: Understanding their relation," Science (1996);272:54-60.
Aidoo et al. "Identification of conserved antigenic components for a cytotoxic T lymphocyte-inducing vaccine against malaria," Lancet (1995);345:1003-1007.
Andersen et al. "Recall of long-lived immunity to *Mycobacterium tuberculosis* infection in mice," J. Immunol. (1995);154:3359-3372.
Billman-Jacobe et al. "Mapping of the T and B cell epitopes of the *Mycobacterium bovis* protein, MPB70," Immunol. Cell Biol. (1990);68:359-365.
Brandt et al. "Key epitopes on the ESAT-6 antigen recognized in mice during the recall of protective immunity to *Mycobacterium tuberculosis*," J. Immunol. (1996);157:3527-3533.
Carrara et al. "Use of a T cell-based assay for monitoring efficacy of antituberculosis therapy," Clin. Infect. Dis. (2004);38:754-756.
Coghlan "Tuberculosis testing finally moves into the $21^{st}$ century," New Scientist (2003);2390:21.
Cooper "The eukaryotic cell cycle" in Chapter 14 of the Cell: A Molecular Approach, $2^{nd}$ Ed., Sinauer Associates, 6 pages (2000).
CSL Biosciences "QuantiFERON-TB™," Direction circular, 19 pages (1994).
De Groote et al. "Novel method for the measurement of cytokine production by a one-stage procedure," J. Immunol. Meth. (1993);163:259-267.
Di Fabio et al. "Quantitation of human influenza virus-specific cytotoxic T lymphocytes: Correlation of cytotoxicity and increased numbers of IFN-γ producing $CD8^+$ T cells," Int'l Immunol. (1994);6:11-19.
ElGhazali et al. "Number of interleukin-4- and interferon-γ-secreting human T cells reactive with tetanus toxoid and te mycobacterial antigen PPD or phytohemagglutinin: Distinct response profiles depending on the type of antigen used for activation," Eur. J. Immunol. (1993);23:2740-2745.
ElGhazali et al. "Comparison of the number of IL-4 and IFN-γ secreting cells in response to the malaria vaccine candidate antigen Pf155/RESA in two groups of naturally primed individuals living in a malaria endemic area in a burkina faso," Scand. J. Immunol. (1995);42:39-45.
Ellefsen et al. "Distribution and functional analysis of memory antiviral CD8 T cell responses in HIV-1 and cytomegalovirus infections," Eur. J. Immunol. (2002);32:3756-3764.
Epstein et al. "The interaction of human macrophages and lymphocytes in the phytohemagglutinin-stimulated production of interferon," J. Clin. Invest. (1971);50:744-753.
European Search Report for divisional EP 01109298.8, 3 pages (2001).
European Search Report for related EP 01109290, two pages, completed Sep. 2001.

(Continued)

*Primary Examiner* — Stacy B. Chen
(74) *Attorney, Agent, or Firm* — Baker Botts, L.L.P.

(57) ABSTRACT

A method of assaying for peptide-specific T-cells comprises adding peptide to a fluid sample of fresh peripheral blood mononuclear cells, and detecting a cytokine such as interferon-γ produced by T-cells that have been pre-sensitized to the peptide. The assay method is quick and cheap and is expected to be useful for the study of various disease states including Hepatitis B, Hepatitis C, tuberculosis, malaria, HIV and influenza.

9 Claims, 4 Drawing Sheets

(56) References Cited

OTHER PUBLICATIONS

Ewer et al. "Comparison of T-cell-based assay with tuberculin skin test for diagnosis of *Mycobacterium tuberculosis* infection in a school tuberculosis outbreak," Lancet (2003);361:1168-1173.
Faguet "Mechanisms of lymphocyte activation. Binding kinetics of phytohemagglutinin to human lymphocytes," J. Biol. Chem. (1977);252:2095-2100.
Falk et al. "Identification of naturally processed viral nonapeptides allows their quantification in infected cells and suggests an allele-specific T cell epitope forecast," J. Exp. Med. (1991);174:425-434.
Falk et al. "Pool sequencing of natural HLA-DR, DQ, and DP ligands reveals detailed peptide motifs, constraints of processing, and general rules," Immunogenetics (1994);39:230-242.
Forsberg et al. "The outer surface proteins of Lyme disease *Borrelia spirochetes* stimulate T cells to secrete interferon-γ (IFN-γ): Diagnostic and pathogenic implications," Clin. Exp. Immunol. (1995);101:453-460.
Goff "Effect of dexamethasone treatment of tuberculous cattle on results of the γ-interferon test for *Mycobacterium bovis*," Immunol. Immunopathol. (1996);53:39-47.
Hagiwara et al. "Effect of HIV infection on the frequency of cytokine-secreting cells in human peripheral blood," AIDS Res. Hum. Retro. (1996);12:127-133.
Hammer et al. "Identification of a motif for HLA-DR1 binding peptides using M13 display libraries," J. Exp. Med. (1992);176:1007-1013.
Hammer et al. "Promiscuous and allele-specific anchors in HLA-DR-binding peptides," Cell (1993);74:197-203.
Hammer et al. "Precise prediction of major histocompatibility complex class II-peptide interaction based on peptide side chain scanning," J. Exp. Med. (1994);180:2353-2358.
Herr et al., "Detection and quantification of blood-derived DC8+ T lymphocytes secreting tumor necrosis factor in response to HLA-A2.1—binding melanoma and viral peptide antigens," Journal of Immuniological Methods (1996);191:131-142.
Herr et al., "The use of computer-assisted video image analysis for the quantification of CD8+ T lymphocytes producing tumor necrosis factor and spots in response to peptide antigens," Journal of Immunological Methods, (1997);203:141-152.
Hill et al. "Molecular analysis of the association of HLA-B53 and resistance to severe malaria," Nature (1992);360:434-439.
Hislop et al. "EBV-specific CD8 T cell memory: Relationships between epitope specificity, cell phenotype, and immediate effector function," J. Immunol. (2001);167:2019-2029.
Huang et al. "Oxidized LDL induces enhanced antibody formation and MHC class II-dependent IFN-γ production in lymphocytes from healthy individuals," Arteriosclerosis, Thrombosis, and Vascular Biology (1995);15:1577-1583.
Int'l Preliminary Examination Report for PCT/GB97/03222, 10 pages (1999).
Int'l Preliminary Examination Report for PCT/GB97/03222, ten pages, completed Feb. 1999.
Int'l Search Report for PCT/GB97/03222, 3 pages (1998).
Int'l Search Report for PCT/GB97/03222, three pages, completed Mar. 1998.
James "Measurements of basic immunologic characteristics of human mononuclear cells," Current Protocols in Immunology, Coligan et al. (eds.), John Wiley, (1994);7.10.1-7.10.10.
Janeway "Characterization of lymphocyte specificity, frequency, and function," in Immunobiology, Fifth Ed., Garland Science, six pages of text, Fig. A.28, and Fig. A.29 (2001).
Jones et al. "Removal of false-positive reactions from plasma in an enzyme immunoassay for bovine interferon-γ," J. Immunol. Meth. (1992);155:233-240.
Kabilan et al. "Detection of intracellular expression and secretion of interferon-γ at the single-cell level after activation of human T cells with tetanus toxoid in vitro," Eur. J. Immunol. (1990);20:1085-1089.
Kalams et al. "Longitudinal analysis of T cell receptor (TCR) gene usage by human immunodeficiency virus 1 envelope-specific cytotoxic T lymphocyte clones reveals a limited TCR repertoire," J. Exp. Med. (1994);179:1261-1271.
Klinman et al. "ELISPOT assay to detect cytokine-secreting murine and human cells" Current Protocols in Immunology, Coligan et al. (eds.), John Wiley, (1994);6.19.1-6.19.8.
Klinman et al. "Activation of interleukin 4- and interleukin 6-secreting cells by HIV-specific synthetic peptides," AIDS Res. Hum. Retro. (1995);11:97-105.
Kruisbeek et al. "Proliferative assays for T cell function," Current Protocols in Immunology, Coligan et al. (eds.), John Wiley, (2004);3.12.1-3.12.20.
Kündig et al. "On the role of antigen in maintaining cytotoxic T-cell memory" Proc. Natl. Acad. Sci. USA (1996);93:9716-9723.
Lalvani et al. "An HLA-based approach to the design of a CTL-inducing vaccine against *Plasmodium falciparium*," Res. Immunol. (1994);145:461-468.
Lalvani et al. "Rapid effector function in CD8+ memory T cells" J. Exp. Med. (1997);186:859-865.
Lalvani et al. "Human cytolytic in interferon γ-secreting CD8+ T lymphocytes" Proc. Natl. Acad. Sci. USA (1998);95:270-275.
Lalvani et al. "Potent induction of focused Th1-Type cellular and humoral immune responses by RTS,S/SBAS2, a recombinant *Plasmodium falciparum* malaria vaccine," J. Infect. Des. (1999);180:1656-1664.
Lalvani et al. "Rapid detection of *Mycobacterium tuberculosis* infection by enumeration of antigen-specific T cells," Am. J. Respir. Crit. Care Med. (2001);163:824-928.
Lalvani et al. "Enhanced contact tracing and spatial tracking of *Mycobacterium tuberculosis* infection by enumeration of antigen-specific T cells," Lancet (2001);357:2017-2021.
Lalvani et al. "Authors' reply," Lancet (2003);361:2082-2083.
Lalvani et al. "Counting antigen-specific T cells: A new approach for monitoring response to tuberculosis treatment?" Clin. Infect. Dis. (2004);38:757-759.
Link et al. "Acetylcholine receptor-reactive T and B cells in myasthenia gravis and controls," J. Clin. Invest. (1991);87:2191-2196.
Lu et al. "Interferon γ- and interleukin-4-secreting cells in multiple sclerosis," J. Neuroimmunol. (1993);46:129-136.
Mackay "Immunological memory," Adv. Immunol. (1993);53:217-265.
Mackay "Immunology: Dual personality of memory T cells," Nature (1999);401:659-660.
McMichael et al. "A new look at T cells," J. Exp. Med. (1998);187:1367-1371.
Mehra et al. "Immune response to recombinant mycobacterial proteins in patients with tuberculosis infection and disease" J. Infect. Dis. (1996);174:431-434.
Milligan et al. "Analysis of herpes simplex virus-specific T cells in the murine female genital tract following genital infection with herpes simplex virus type 2," (1995);Virology 212:481-489.
Minutes of Oral Proceeding before the Opposition Division in EP 0941478 (2005).
Miyahira et al. "Quantification of antigen specific CD8+ T cells using an Elispot assay,"J. Immunol. Meth. (1995);181:45-54.
Müller et al. "Expansion of γ interferon-producing CD8 T cells following secondary infection of mice immune to *Leishmania major*," Infect. Immun. (1994);62:2575-2581.
Oxford Immunotec "New TB test brings tuberculosis care into 21$^{st}$ century," Press release, 3 pages (1994).
Oxford Immunotec "T SPOT-TB" Instructions for use, 5 pages (1994).
Oxford Immunotec "Summary of clinical trials completed using T SPOT-TB" 2 pages (1994).
Pamer et al. "Precise prediction of a dominant class I MHC-restricted epitope of *Listeria monocytogenes*," Nature (1991);353:852-855.
Pathan et al. "Direct ex vivo analysis of antigen-specific IFN-γ-secreting CD4 T cells in *Mycobacterium tuberculosis*-infected individuals: Associations with clinical disease state and effect of treatment," J. Immunol. (2001);167:5217-5225.
Pollock et al. "Peptide mapping of bovine T-cell epitopes for the 38 kDa tuberculosis antigen," Scand. J. Immunol. (1995);41:85-93.

(56) References Cited

OTHER PUBLICATIONS

Rammensee et al. "MHC ligands and peptide motifs: First listing," Immunogenetics (1995);41:178-228.

Rothel et al. "Analysis of polyclonal T-cell determinants on the *Mycobacterium bovis* secretory protein MPB-70," Vaccines 90, Lome (Program and Abstracts) Abstract E42 (1990).

Rothel et al. "A sandwich enzyme immunoassay for bovine interferon-γ and its use for the detection of tuberculosis in cattle," Austral. Vet. J. (1990);67:134-137.

Rothel et al. "The γ-interferon assay for diagnosis of bovine tuberculosis in cattle: Conditions affecting the production of γ-interferon in whole blood culture," Austral. Vet. J. (1992);69:1-4.

Sallusto et al. "Two subsets of memory T lymphocytes with distinct homing potentials and effector functions," Nature (1999);401:708-712.

Scheibenbogen et al. "CD8 T-cell responses to Wilms tumor gene product WT1 and proteinase 3 in patients with acute myeloid leukemia," Blood (2002);100:2132-2137.

Sørensen et al. "Purification and characterization of a low-molecular-mass T-cell antigen secreted by *Mycobacterium tuberculosis*," Infect. Immun. (1995);63:1710-1717.

Surcel et al. "Th1/Th2 profiles in tuberculosis, based on the proliferation and cytokine response of blood lymphocytes to mycobacterial antigens," Immunol. (1994);81:171-176.

Taguchi et al. "Detection of individual mouse splenic T cells producing IFN-γ and IL-5 using the enzyme-linked immunospot (ELISPOT) assay," J. Exp. Med. (1990);128:65-73.

Valentine et al. "Phytohemagglutinin binds to the 20-kDa molecule of the T3 complex," Eur. J. Immunol. (1985);15:851-854.

Vincenti et al. "Identification of early secretory antigen target-6 epitopes for the immunodiagnosis of active tuberculosis," Mol. Med. (2003);9:105-111.

Wang et al. "Lyme neuroborreliosis: Evidence of persistent up-regulation of *Borrelia burgdorferi*-reactive cells secreting interferon-γ," Scand. J. Immunol. (1995);42:694-700.

Whipple et al. "Comparison of the sensitivity of the caudal fold skin test and commercial γ-interferon assay for diagnosis of bovine tuberculosis," Am. J. Vet. Res. (1995);56:415-419.

Wilkinson et al. "38000 MW antigen-specific major histocompatibility complex class I restricted interferon-γ-secreting CD8[+] T cells in healthy contacts of tuberculosis," Immunol. (1998);95:585-590.

Wood et al. "Epitope mapping of the polyclonal bovine T and B cell response to a mycobacterial protein," Frontiers in Mycobacteriology: Immunology of Mycobacterial Infections, Vail, Colorado, Abstract 9 (1990).

Wood et al. "Development of a simple, rapid in vitro cellular assay for bovine tuberculosis based on the production of γ interferon," Res. Vet. Sci. (1990);49:46-49.

Wood et al. "Field comparison of the interferon-γ assay and the intradermal tuberculin test for the diagnosis of bovine tuberculosis," Austral. Vet. J. (1991);68:286-290.

Wood et al. "A field evaluation of serological and cellular diagnostic tests for bovine tuberculosis," Vet. Microbiol. (1992);31:71-79.

Written Decision of the Opposition Division in EP 0941478 (2005).

Yi et al. "Idiotype-reactive T-cell subsets and tumor load in monoclonal gammopathies," Blood (1995);86:3043-3049.

\* cited by examiner

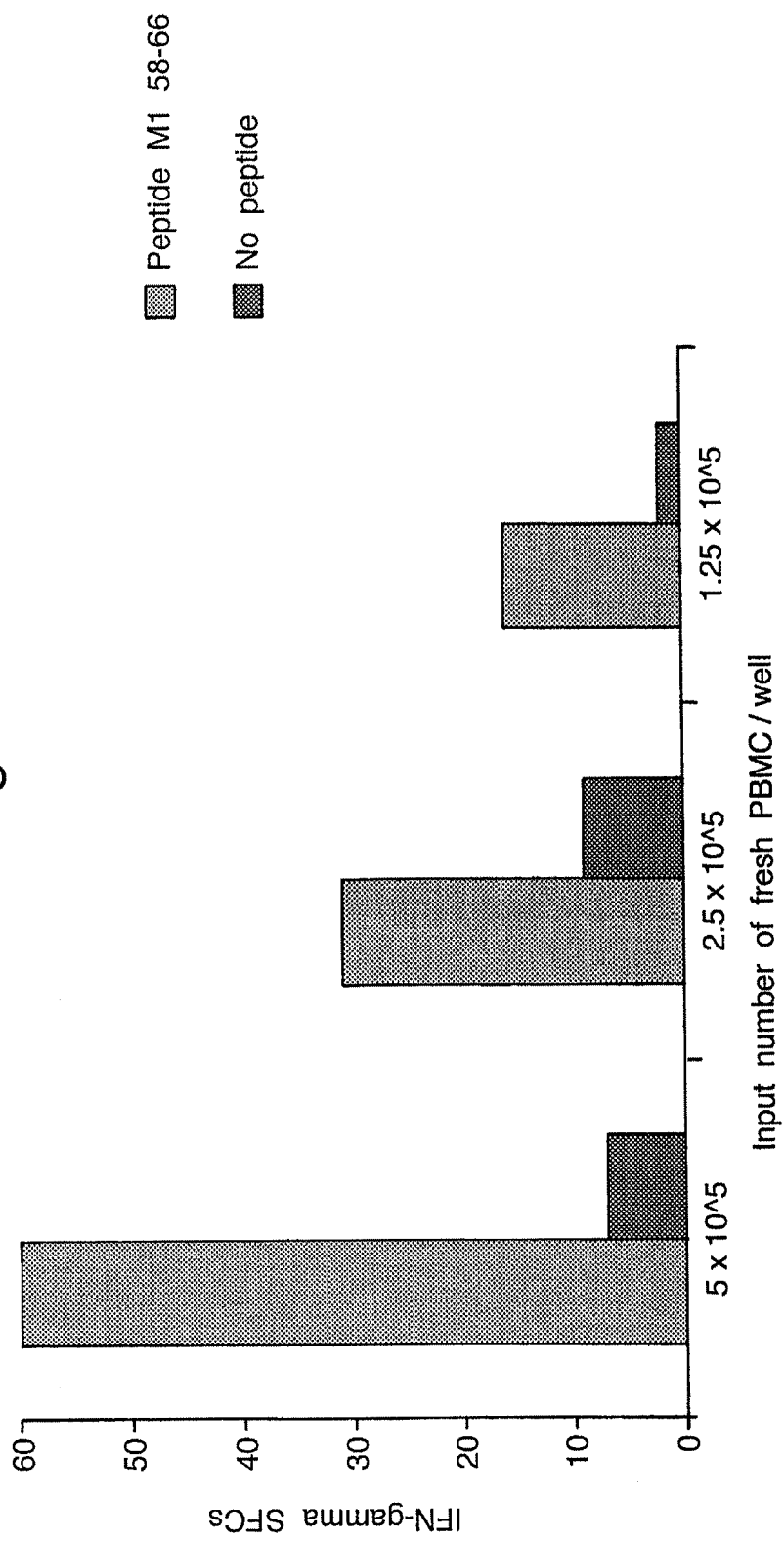

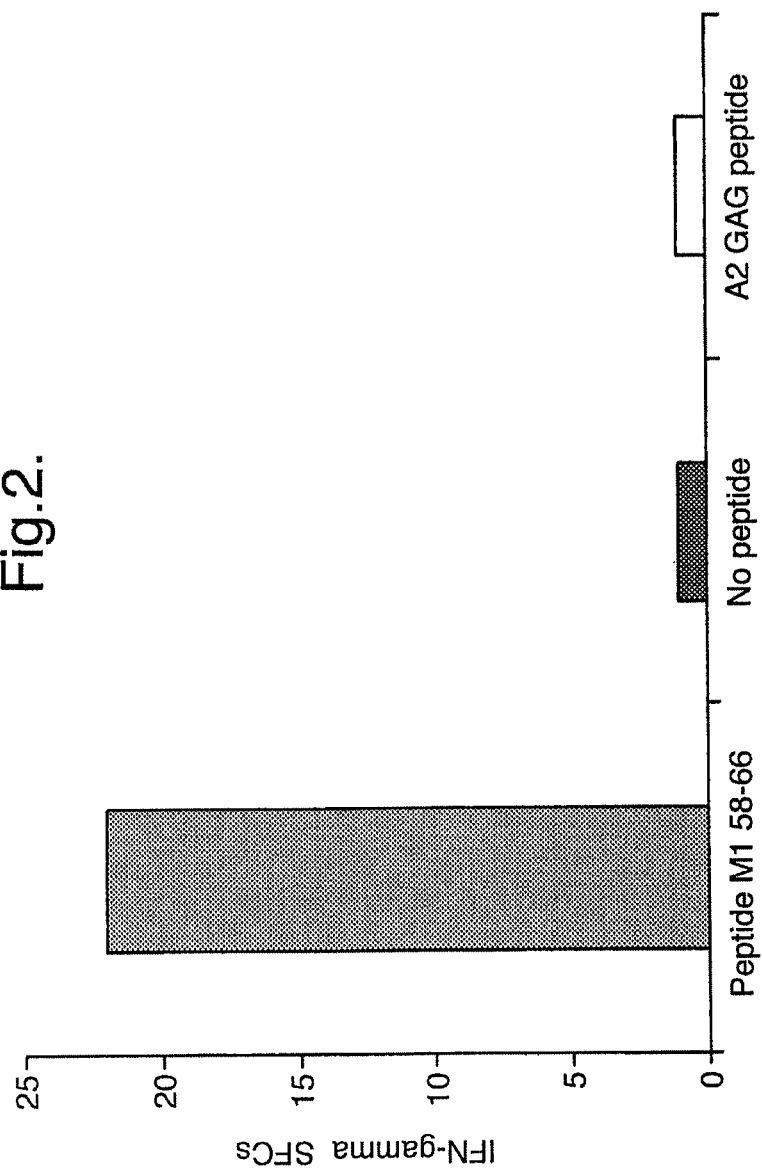

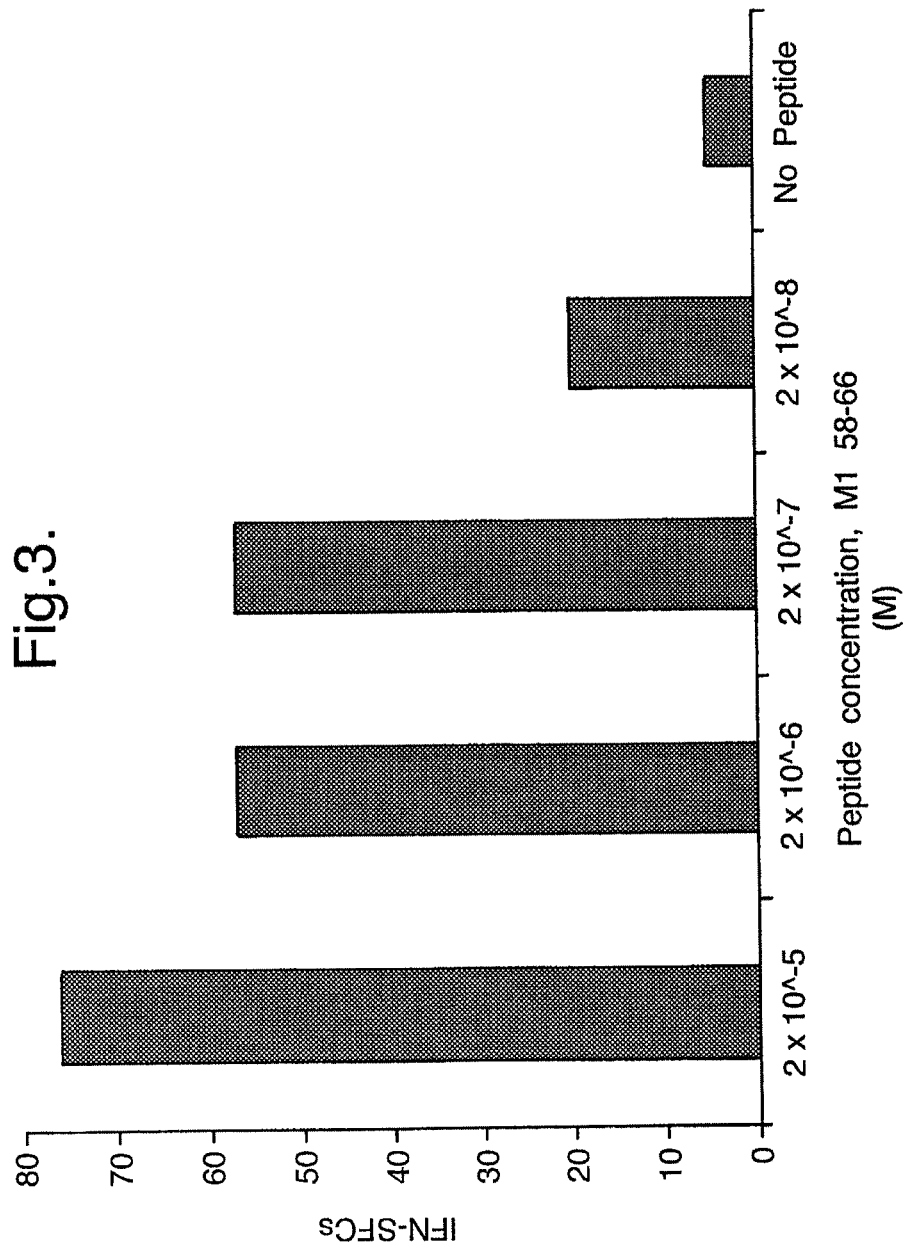

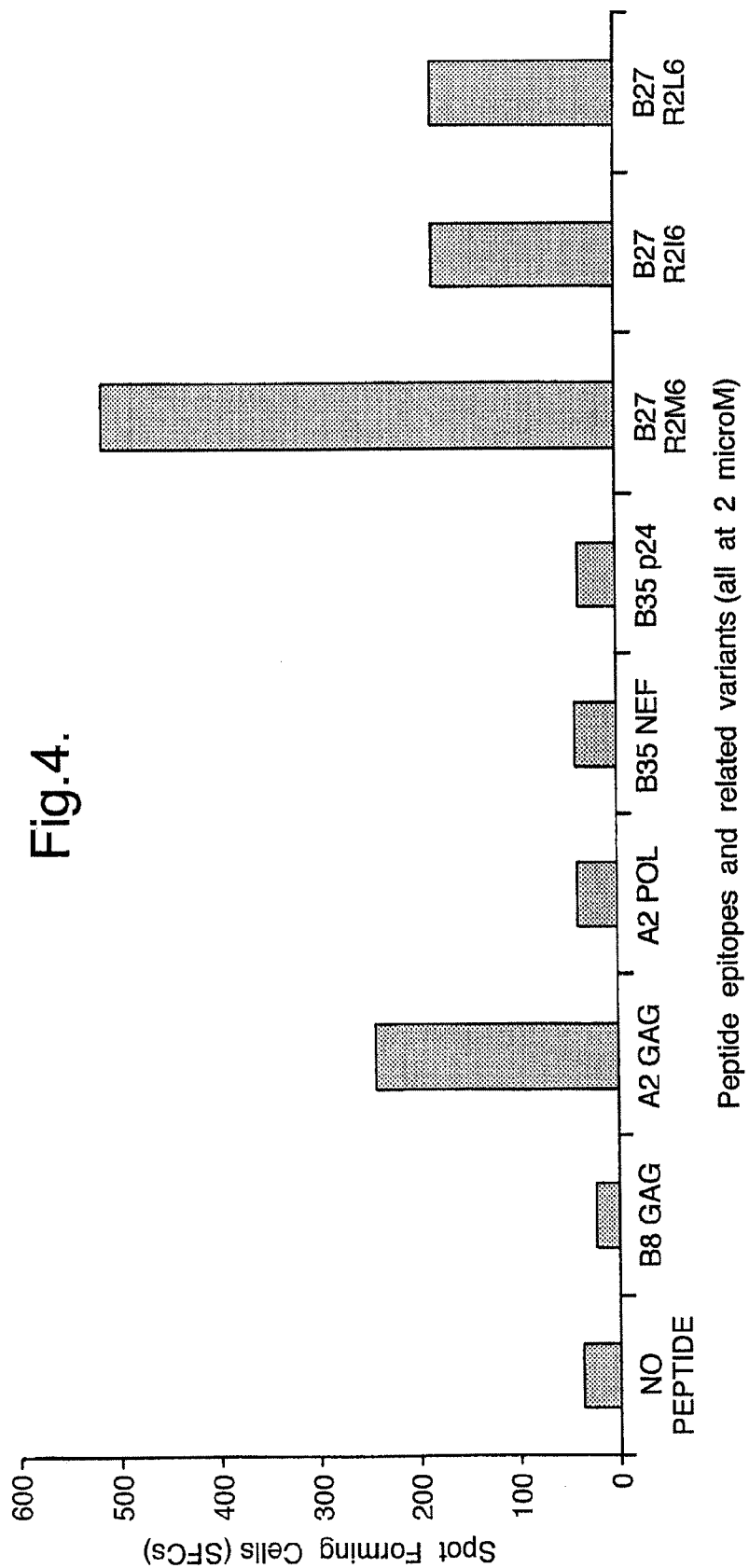

SEQUENCE LISTING

<160> NUMBER OF SEQ ID NOS: 12

<210> SEQ ID NO 1
<211> LENGTH: 9
<212> TYPE: PRT
<213> ORGANISM: Artificial Sequence
<220> FEATURE:
<223> OTHER INFORMATION: M1 58-66 peptide

<400> SEQUENCE: 1

Gly Ile Leu Gly Phe Val Phe Thr Leu
1               5

<210> SEQ ID NO 2
<211> LENGTH: 9
<212> TYPE: PRT
<213> ORGANISM: Artificial Sequence
<220> FEATURE:
<223> OTHER INFORMATION: NP 380-388 peptide

<400> SEQUENCE: 2

Glu Leu Arg Ser Arg Tyr Trp Ala Ile
1               5

<210> SEQ ID NO 3
<211> LENGTH: 8
<212> TYPE: PRT
<213> ORGANISM: Artificial Sequence
<220> FEATURE:
<223> OTHER INFORMATION: M1 128-135 peptide

<400> SEQUENCE: 3

Ala Ser Cys Met Gly Leu Ile Tyr
1               5

<210> SEQ ID NO 4
<211> LENGTH: 9
<212> TYPE: PRT
<213> ORGANISM: Artificial Sequence
<220> FEATURE:
<223> OTHER INFORMATION: NP 265-273 peptide

<400> SEQUENCE: 4

Ile Leu Arg Gly Ser Val Ala His Lys
1               5

<210> SEQ ID NO 5
<211> LENGTH: 9
<212> TYPE: PRT
<213> ORGANISM: Artificial Sequence
<220> FEATURE:
<223> OTHER INFORMATION: NP 383-391 peptide

<400> SEQUENCE: 5

Ser Arg Tyr Trp Ala Ile Arg Thr Arg
1               5

<210> SEQ ID NO 6
<211> LENGTH: 9
<212> TYPE: PRT
<213> ORGANISM: Artificial Sequence
<220> FEATURE:
<223> OTHER INFORMATION: ES8 peptide

<400> SEQUENCE: 6

Gly Ile Glu Ala Ala Ala Ser Ala Ile

```
1               5

<210> SEQ ID NO 7
<211> LENGTH: 9
<212> TYPE: PRT
<213> ORGANISM: Artificial Sequence
<220> FEATURE:
<223> OTHER INFORMATION: ES9 peptide

<400> SEQUENCE: 7

Ala Ile Gln Gly Asn Val Thr Ser Ile
1               5

<210> SEQ ID NO 8
<211> LENGTH: 9
<212> TYPE: PRT
<213> ORGANISM: Artificial Sequence
<220> FEATURE:
<223> OTHER INFORMATION: ES10 peptide

<400> SEQUENCE: 8

Leu Leu Asp Glu Gly Lys Gln Ser Leu
1               5

<210> SEQ ID NO 9
<211> LENGTH: 9
<212> TYPE: PRT
<213> ORGANISM: Artificial Sequence
<220> FEATURE:
<223> OTHER INFORMATION: ES11 peptide

<400> SEQUENCE: 9

Glu Leu Asn Asn Ala Leu Gln Asn Leu
1               5

<210> SEQ ID NO 10
<211> LENGTH: 9
<212> TYPE: PRT
<213> ORGANISM: Artificial Sequence
<220> FEATURE:
<223> OTHER INFORMATION: ES13 peptide

<400> SEQUENCE: 10

Ala Met Ala Ser Thr Glu Gly Asn Val
1               5

<210> SEQ ID NO 11
<211> LENGTH: 9
<212> TYPE: PRT
<213> ORGANISM: Artificial Sequence
<220> FEATURE:
<223> OTHER INFORMATION: ES7 peptide

<400> SEQUENCE: 11

Glu Gly Lys Gln Ser Leu Thr Lys Leu
1               5

<210> SEQ ID NO 12
<211> LENGTH: 8
<212> TYPE: PRT
<213> ORGANISM: Artificial Sequence
<220> FEATURE:
<223> OTHER INFORMATION: ES12 peptide

<400> SEQUENCE: 12

Leu Gln Asn Leu Ala Arg Thr Ile
1               5
```

ASSAY METHOD FOR PEPTIDE SPECIFIC T-CELLS

CROSS REFERENCE TO RELATED APPLICATIONS

This application is a continuation of U.S. patent application Ser. No. 09/308,725 filed May 24, 1999, issued on Aug. 18, 2009 as U.S. Pat. No. 7,575,870, which is a continuation of International Patent Application No. PCT/GB97/03222 filed Nov. 25, 1997 and published as WO 98/23960, which claims priority to British Application No. 9624456.1 filed Nov. 25, 1996, the contents of each of which are incorporated herein by reference in their entireties.

SEQUENCE LISTING

The specification further incorporates by reference the Sequence Listing submitted herewith via EFS on Jul. 28, 2009. Pursuant to 37 C.F.R. §1.52(e)(5), the Sequence Listing text file, identified as 0775290118seqlist.txt, is 2,156 bytes and was created on Jul. 24, 2009.

This invention is concerned with a method of assaying for activated peptide-specific T-cells. It is a development of the known ELISPOT assay, which is reviewed in current protocols in Immunology, Unit 6.19, pages 6.19.1-8.

The filter immunoplaque assay, otherwise called the enzyme-linked immunospot assay (ELISPOT), was initially developed to detect and quantitate individual antibody-secreting B cells. At the time it was developed, the technique provided a rapid and versatile alternative to conventional plaque-forming cell assays. Recent modifications have improved the sensitivity of the ELISPOT assay such that cells producing as few as 100 molecules of specific protein per second can be detected. These assays take advantage of the relatively high concentration of a given protein (such as a cytokine) in the environment immediately surrounding the protein-secreting cell. These cell products are captured and detected using high-affinity antibodies.

The ELISPOT assay utilises two high-affinity cytokine-specific antibodies directed against different epitopes on the same cytokine molecule: either two monoclonal antibodies or a combination of one monoclonal antibody and one polyvalent antiserum. ELISPOT generates spots based on a calorimetric reaction that detects the cytokine secreted by a single cell. The spot represents a "footprint" of the original cytokine-producing cell. Spots are permanent and can be quantitated visually, microscopically, or electronically.

The ELISPOT assay involves five specific steps: (1) coating a purified cytokine-specific antibody to a nitrocellulose-backed microtitre plate; (2) blocking the plate to prevent nonspecific absorption of any other proteins, (3) incubating the cytokine-secreting cells at several different dilutions; (4) adding a labelled second anti-cytokine antibody; and (5) detecting the antibody-cytokine complex.

In this invention, the technique has been used to develop an assay for peptide-specific T-cells that have been pre-sensitised in vivo to a particular peptide.

Thus the present invention provides a method of assaying for peptide-specific T-cells, which method comprises providing a fluid containing T-cells, adding a peptide to the fluid, incubating the fluid to cause cytokine release, and detecting the released cytokine. Preferably the method comprises providing the fluid containing T-cells in contact with a surface carrying an immobilised first antibody to the cytokine, adding the peptide to the fluid, incubating the resulting fluid mixture under conditions to cause any peptide-specific T-cells that have been pre-sensitised in vivo to the peptide to secrete the cytokine, and detecting any secreted cytokine bound to the immobilised first antibody.

The cells are preferably peripheral blood mononuclear cells (PMBC). They may suitably be taken from a patient known to be suffering, or to have suffered, from an infection with an intracellular pathogen, e.g. a virus. It is a preferred feature of the invention that fresh cells are used, because cells cultured in vitro may develop altered characteristics thus reducing the diagnostic value of the assay. The purpose of the assay is to identify or quantitate peptide-specific T-cells e.g. CD8+ or CD4+ cells that have been activated or pre-sensitised in vivo to a particular peptide. These are unrestimulated T-cells, i.e. cells capable of immediate effector function without the need to effect division/differentiation by in vitro culture. When the peptide in question is presented to such cells, the cells secrete various cytokines, of which any one may be selected for the purposes of this assay. Preferably the cytokine selected is interferon-γ (IFN γ).

The secreted cytokine can be detected by any of a variety of methods known in the literature. Preferably the assay method involves providing a surface carrying an immobilised first antibody to the IFN-γ or other cytokine. A fluid containing the PBMC or other fresh cells is placed in contact with that immobilised antibody. About 30% of the PBMC are CD8+ cells. In the PBMC of a patient who has recovered from a previous influenza virus infection, about 1 CD8+ cell in $10^5$-$10^6$ is a memory cell that has been pre-sensitised to a specific epitope associated with the influenza virus.

The method of the invention involves adding a peptide to the fluid. The peptide may be a known epitope for a well characterised viral infection; or may be a candidate epitope possibly associated with a less well characterised viral infection. The resulting fluid mixture is incubated under conditions to stimulate any peptide-specific T-cells that may have been pre-sensitised to that particular virus-derived peptide in vivo. The peptide needs to be of a length, e.g. 7-15 and particularly 8-12 or 8-10 amino acid residues long, that is recognised by CD8+ cells. It is supposed that the generality of the CD8+ cells (and other PBMC) present the peptide to the small minority of CD8+ cells that may have been pre-sensitised to the peptide. If such activated or pre-sensitised peptide-specific T-cells are present in the test fluid, they respond by secreting IFN-γ or other cytokine which then becomes bound to the immobilised antibody.

It is preferred that the peptide be added in uncombined form to the fresh cells. While it is possible to add cultured cells that have been pulsed with the peptide, this is not necessary when using defined peptide epitopes. The peptides should be added in an amount sufficient to generate an observable signal; a preferred concentration range in the fluid is 0.01 up to 100 μM particularly 0.5-5.0 μM.

Incubation should be continued for a time sufficient to permit CD8+ cells that have been pre-sensitised in vivo to the particular peptide chosen to secrete the IFN-γ or other cytokine. The incubation should not continue for so long that quiescent CD8+ cells have time to differentiate and become activated by the peptide and start to secrete cytokines. This suggests an incubation time of 4-24 hours, more particularly 6-16 hours. It is an advantage of the invention that the incubation part of the test can be performed in a single working day or overnight, and without the use of sterile conditions required for cell culture in vitro.

During the incubation, any IFN-γ or other cytokine secreted by CD8+ cells becomes bound to the first antibody immobilised on the surface. After incubation, the surface may be washed to remove unbound material. For detection, preferably a labelled second antibody to the cytokine is used. When this is applied to the surface it becomes bound to any cytokine present. The second antibody should preferably recognise a different epitope from the first antibody. One or both of the first and second antibodies should preferably be monoclonal. The label may be any that is conventionally used in the field, including radioisotopes, enzymes to generate colour or chemiluminescence, fluorescent groups or groups for detection by mass spectrometry or refractive index (e.g. by surface plasmon resonance). It is convenient but not necessary to use a labelled antibody, any reagent that binds specifically to the cytokine could be labelled and used. Detection and perhaps quantitation of the label is effected by means well known in the field and appropriate to the nature of the label used.

The assay may conveniently be carried out in a multiwell plate. Each well of the plate has a surface carrying a bound first antibody. To each well is added a fluid containing an appropriate number, e.g. $10^3$-$10^6$ of cells. Different peptides and/or controls are added to individual wells of the plate. Cells that secrete a cytokine during incubation show up as spots (spot forming cells or SFCs) and the number or density of these in each well can readily be determined.

The assay technique has a number of advantages over prior known techniques:— a) It is quicker and more convenient; the duration of the assay is only 6 hours and thus does not require sterile conditions or technique. Current methods of enumerating precursor effector T cells require in vitro culture with the specific antigen and autologous feeder cells in a limiting dilution assay (LDA). The method is laborious and time consuming.

b) It requires minimal technical equipment and is suitable for field conditions in the tropics and developing countries as well as routine diagnostic laboratories. The LDA, by contrast, requires many peripheral blood lymphocytes, a source of gamma irradiation to inactivate the feeder cells and sterile conditions, as the cells need to be cultured for 1-2 weeks.

c) It is safe and non-radioactive. In the LDA, however, the cultured cells are assayed in a cytotoxic T cell assay (CTL) assay using the radioactive isotope chromium-51.

d) It is an immediate ex vivo assay. As such it measures effector cells in their natural state without the introduction of unknown biases that occur as cells proliferate in vitro culture with antigen and exogenous cytokines.

e) The assay is performed over only 6 hours; as such it measures peptide-specific effector cells directly, without requiring these cells to proliferate in vitro. The short duration of the assay also eliminates the possibility that the cells may be becoming activated in vitro; it therefore measures effector function that is present in vivo. LDAs require the cells to proliferate many fold; however many effector cells do not proliferate in these conditions and therefore the result of the LDA is often an underestimate of the true number of circulating effectors.

The assay technique is expected to be of value in a number of different ways:— i) For research into the mechanisms involved in peptide presentation and recognition and activation. Through the experimental work described in outline below, the inventors have gained insight into the phenotype and effector function of antigen-specific T-cells freshly isolated from peripheral blood have been investigated.

ii) For quantifying peptide-specific effectors in HIV-infected individuals direct from peripheral blood.

iii) For monitoring the progress of, or resistance to, a chronic infectious disease, for example in response to a drug or therapeutic vaccine. This is expected to be particularly useful for HIV, Hepatitis B and Hepatitis C.

iv) For identifying peptides that may be implicated in a disease state (Epitope mapping), an important preliminary step in the design of a new vaccine. This is expected to be of interest for tuberculosis, malaria and HIV.

v) For monitoring the extent to which a patient, who has suffered from a particular disease such as influenza, may be resistant to future infections.

vi) For monitoring induction and maintenance of CD8+ and CD4+ antigen-specific T cells following immunization with experimental preventative vaccines, e.g. malaria.

The following examples illustrate the invention with reference to the following figures.

BRIEF DESCRIPTION OF THE DRAWINGS

FIG. 1 shows the response of PBMCs at different cell concentrations to an HLA class I-restricted epitope, namely influenza T cell epitope M1 58-66, following a 12-14 hour incubation.

FIG. 2 shows the enumeration of IFN-γ releasing spot-forming cells (SFCs) for the same epitope as used for FIG. 1 following a six hour incubation.

FIG. 3 shows the enumeration of IFN-γ releasing SFCs for the same epitope at different concentrations of the same epitope used for FIG. 1.

FIG. 4 shows the enumeration of IFN-γ releasing SFCs following stimulation for 12 hours with various peptide epitopes derived from HIV proteins.

EXAMPLE 1

Immunological Memory to Influenza Virus

Ex Vivo Enumeration and Characterisation of Circulating Peptide-Specific CD8+ Activated T Cells in the Memory State Subjects were healthy laboratory personnel or healthy adult volunteers, who were HLA typed serologically by complement mediated lymphocytotoxicity. 5 MHC Class I-restricted influenza epitopes were used and are listed in Table 1.

96-well PVDF-backed plates were coated with 100 μl of 15 μg/ml of the anti-IFN-γ Mab 1-DIK overnight at 4° or at room temperature for 3 hours. The plates were washed and then blocked with R10 (standard tissue culture medium containing 10% fetal calf serum) for 1 hour at room temperature. PBMC of the subjects were separated from heparinised whole blood by centrifugation, resuspended in R10 and added in a final volume of 100 μl R10/well to the 96-well PVDF backed microtitre plates. Input cell numbers were usually 5×$10^5$ per well, and all assays were done in duplicate wells. Peptides were usually added to a final concentration of 1-2 μM, except in one peptide titration experiment where the concentration of the M1 58-66 peptide was diluted to 20 nM. Assays were usually performed for 12-14 hours, but certain assays were performed for 6 hours to confirm that the antigen-specific cells were capable of immediate effector function. Incubation was carried out at 37° C. in an atmosphere containing 5% $CO_2$. Incubation was arrested by shaking off the contents of the wells and washing. Then 100 μl of 1 μg/ml of a biotinylated second anti-IFN-γ MAB 7-B6-1-biotin (Mabtech, Stockholm, Sweden) was added to the wells and the plates incubated for 3 hours. 100 μl of 1:1000 dilution of streptavidin-alkaline phosphatase conjugate was added to the wells and the plates incubated at room temperature for a further 2 hours. The wells were again washed, and 100 μl of chromogenic alkaline phosphatase substrate diluted 1:25 with deionised water was added to the wells. After a further 30-60 minutes incubation at room temperature the wells were washed to terminate the colorimetric reaction. The spots were counted under ×20 magnification with a dissecting stereomicroscope.

Results

Using 5 well-defined HLA Class I-restricted influenza epitopes, free peptide was added to a final concentration of 2 μm directly to the freshly isolated PBMC in the ELISPOT assay. For almost all the individuals tested in this way, using epitopes restricted by HLA Class I alleles present in the individual, IFN-γ secreting peptide-specific effector T-cells were detected. Table 1 summarises the responses to these five epitopes. Most of these assays were performed over 12-14 hours, and FIG. 1 is a bar chart showing the response at different concentrations of PBMC per well. However, to exclude the possibility that memory T-cells might proliferate or become activated in vitro during the course of a 14 hour assay, 6 hour assays were also performed. Peptide-specific SFCs were detected as shown for the same M1 58-66 epitope quantitatively in FIG. 2. For a negative control, irrelevant peptides from infectious agents which the donor was not infected were added directly to the fresh PBMC.

Most experiments were performed at final peptide concentrations of 2 μm. However, responses were still readily detectable when peptide concentrations were reduced down to 0.02 μm, as shown in FIG. 3 for the influenza HLA-A2.01-restricted matrix epitope.

Depletion of CD8+ T-cells from fresh PBMC with anti-CD8 antibody-coated magnetic beads completely abrogated the peptide-specific response, confirming that the effectors giving rise to the spots elicited by known Class I-restricted epitopes are CD8+ T lymphocytes. Conversely, depletion of CD4+ cells did not diminish the number of IFN-γ SFCs, indicating that neither CD4+ nor their cytokine products were required for the acquisition or deployment of effector function by the freshly isolated peptide-specific CD8+ T cells. Immediate effector responses were only detected to influenza epitopes restricted by the HLA Class I alleles present in the particular donor being tested; addition of influenza epitopes restricted by HLA Class I molecules not present in the donor never resulted in SFCs. (data not shown).

While expansion of peptide-specific CD8+ effector CTL during acute influenza renders the cells detectable by means of the known $^{51}$Cr release cytotoxicity assay performed with fresh uncultured PBMC, after recovery from the acute illness, such cells are no longer detectable. It appears that this is not because they are absent, but rather because they are present at too low a frequency to be detectable. After recovery from the acute illness, such cells remain detectable by the ELISPOT assay technique of the present invention.

Counting the spots under magnification, and comparing this number to the input number of fresh PBMC gives a measure of the relative frequency of circulating activated peptide-specific CD8+ effectors in peripheral blood. The frequency of IFN-γ-secreting CD8+ effectors for the HLA-A2.1-restricted epitope M1 58-56 in donor WB was measured by the invention assay (1/15000) and by conventional limiting dilution analysis (LDA) (1/103000).

TABLE 1

Class I-restricted influenza epitopes recognized by freshly isolated CD8+ effector T cells (SEQ ID NOS: 1-5).

| Protein | Sequence | MHC class I restriction | No of Responders | No of donors tested |
|---|---|---|---|---|
| M1 58-66 | GILGFVFTL (SEQ ID NO: 1) | A2.01 | 6 | 6 |

TABLE 1-continued

Class I-restricted influenza epitopes recognized by freshly isolated CD8+ effector T cells (SEQ ID NOS: 1-5).

| Protein | Sequence | MHC class I restriction | No of Responders | No of donors tested |
|---|---|---|---|---|
| NP 380-388 | ELRSRYWAI (SEQ ID NO: 2) | B8 | 3 | 4 |
| M1 128-135 | ASCMGLIY (SEQ ID NO: 3) | B35 | 2 | 2 |
| NP 265-273 | ILRGSVAHK (SEQ ID NO: 4) | A3 | 1 | 2 |
| NP 383-391 | SRYWAIRTR (SEQ ID NO: 5) | B27.05 | 1 | 1 |

The above experiment is described in greater detail in J. Exp. Med., 186, 6, Sep. 15, 1997, 859-865, which is incorporated herein by reference.

EXAMPLE 2

Application to Quantifying Peptide-Specific Effectors in HIV-Infected Individuals Direct from Peripheral Blood Cryopreserved peripheral blood lymphocytes (PBL) that had been freshly isolated from the peripheral blood of patient 868 were plated out at 50,000 cells per well of a PVDF coated 96 well plate, which had previously been coated with anti-interferon-γ monoclonal antibody. Duplicate wells were set up for each antigen. Two types of duplicate control wells were used: no peptide and an irrelevant HIV gag epitope restricted through HLA-B8, an HLA allele not present in patient 868.

A range of peptides and their respective naturally occurring variants (previously identified in patient 868) were added directly to the cells at a final concentration of 2 μM. The plate was incubated for 12 hrs at 37° C. in 5% $CO_2$ and developed as previously described (see Example 1). The resulting spots were counted with a ×40 dissection microscope. These results are presented in tabular form in FIG. 4.

EXAMPLE 3

Identification of CD4+ and CD8+ Epitopes in Secreted Antigens of M. Tuberculosis Mounting evidence points to a protective role for CD8+ cytotoxic T lymphocytes in Mycobacterium tuberculosis infection, but M. tuberculosis-specific CD8+ T cells have not hitherto been identified in man. Using a reverse immunogenetic approach, the inventors have synthesized an array of candidate HLA Class I restricted peptides from two immunodominant antigens of M. tuberculosis, ESAT-6 and antigen 85. The inventors have screened 75 subjects representing a broad clinical spectrum of M. tuberculosis infection. Peripheral blood lymphocytes were stimulated in vitro with the peptides and then tested for cytotolytic activity in a $^{51}$Cr release assay and for single cell interferon-γ release in an ELISPOT assay. The inventors have identified several octamer and nonamer epitopes from ESAT-6 and antigen 85 in patients and exposed contacts. Certain epitopes are recognised by CD8+ lymphocytes in an MHC Class I restricted manner; others are recognised preferentially by CD4+ T cells.

The sequences of ESAT-6 and antigen 85A, B and C were scanned with allele-specific peptide motifs for the HLA class I types-A2, -B7, -B8, -B35, -B52 and -B53 all of which were present in the study population.

For ESAT-6, sequences congruent with the peptide motifs HLA-A2, -B8 and -B52 were identified; these peptides were synthesized and are displayed in Table 2 (SEQ ID NOS:6-12). No sequences congruent with HLA-B7, -B35 and -B53 were present in ESAT-6 and thus no peptides were synthesized for these HLA class I alleles. Peptides were sorted into pools that were used for in vitro restimulation of donor PBMC. Peptides were found to be CD8+ epitopes are shown in boldface. Similarly, 42 peptides were synthesized based on the sequences of antigens 85A and 85C. No CD8+ epitopes were identified amongst these and the peptides are not shown.

TABLE 2

| HLA class I allele | Peptide motif | Peptide | Sequence | Position |
|---|---|---|---|---|
| HLA-A2 | -L/I/M------V/L/I | ES8 | GIEAAASAI (SEQ ID NO: 6) | 10-18 |
| | | ES9 | AIQGNVTSI (SEQ ID NO: 7) | 17-25 |
| | | ES10 | LLDEGKQSL (SEQ ID NO: 8) | 28-36 |
| | | ES11 | ELNNALQNL (SEQ ID NO: 9) | 64-72 |
| | | ES13 | AMASTEGNV (SEQ ID NO: 10) | 82-90 |
| HLA-B8 | --K-K---L/I | ES7 | EGKQSLTKL (SEQ ID NO: 11) | 31-39 |
| HLA-B52 | -Q-----I/V | ES12 | LQNLARTI (SEQ ID NO: 12) | 69-76 |

ELISPOT Assay for IFN-γ

96-well PVDF-backed plates pre-coated with the anti-IFN-γ mAb 1-DIK at 15 μg/ml were washed with RPMI and blocked with R10 for 1-h at room temperature. In one experiment, 500,000 freshly isolated uncultured PBMC were used per well. In another experiment short term cell lines (STCL) or CD8+ cytotoxic T lymphocytes (CTL) or clones were washed ×2 in RPMI, resuspended in R10, and dispersed at known cell input number/well in duplicate wells. Responses were considered significant if a minimum of 10 SFCs were present per well and additionally this number was at least twice that in control wells. Peptide was added directly to the supernatant at a final concentration of 2 μl (free peptide). Plates were incubated for 12 hrs at 37° C., 5% $CO_2$. After washing ×6 with phosphate buffered saline 0.05% Tween-20 to remove cells, plates were incubated for 3 hrs with the second biotinylated anti-IFN-γ mAb 7-B6-1-biotin at 1 μg/ml. A further wash as above was followed by incubation with a 1:1000 dilution of streptavidin-alkaline phosphatase conjugate for 2 hrs. After another wash, chromogenic alkaline phosphatase substrate was added to the wells and 30 mins. later plates were washed with tap water. After drying, spot forming cells (SFC) were counted under ×20 magnification.

STCL were generated by the method described in Nature 346 (1990) 183-7. CD8+ T-cell clones were generated by standard methods.

Identification of ESAT-6 Specific Effector T Cells Direct from Peripheral Blood.

Two CD8+ epitopes in ESAT-6 were identified. The T cells from donor NPH54, who had tuberculous mediastinal lymphadenitis recognised peptides corresponding to both of these epitopes. Uncultured PBMC isolated at the time of diagnosis from NPH54, who has HLA-B52 and HLA-A2.01, secreted IFN-γ in response to an ESAT-6-derived peptide pool for these class I alleles in an ex vivo ELISPOT assay. The mean number of IFN-γ spot-forming cells (SFCs) enumerated from $5 \times 10^5$ PBMC in duplicate wells was 19 for the ESAT-6 peptides compared to 2 in the control wells with no peptide. A subsequent assay tested freshly isolated PBMC against each of the individual peptides within the responding pools; IFN-γ SFCs were detected in response to peptides ES12 and ES13, whose sequences are congruent with the HLA-B52 and HLA-A2.01 peptide motifs respectively. The frequency of ES12- and ES13-specific IFN-γ SFCs is of the same order of magnitude as SFCs for HLA-A2.01-restricted influenza matrix epitope M1 58-66. Unrestimulated PBMC from a second donor, NPH97, with tuberculous osteomyelitis, also recognised the ES12 peptide. This patient also has HLA-B52 and -A2.01 and the magnitude of the ES12-specific response was similar to the response to the HLA-A2-restricted influenza matrix epitope. Single cell IFN-γ release by freshly isolated T cells in these short 12 hr ex vivo assays, employing no stimulus other than cognate peptide, indicates that these cells are highly likely to be circulating activated effector T cells.

EXAMPLE 4

Application to Malaria

The assay method of this invention has been used effectively to track the induction of antigen-specific cellular immune responses induced by immunisation with a novel malaria vaccine candidate RTS.S. This vaccine candidate includes most but not all of the peptide sequence of the circumsporozoite protein (CSP) antigen, a 412 amino acid protein. PMBC of 10 healthy volunteers were obtained and analysed before, during and after a standard three-dose vaccination. 25 15-mer peptides spanning the entire amino acid sequence of the CSP antigen contained in RTS.S were used to detect epitope specific T-cells. An ex vivo ELISPOT assay for IFN-γ was performed, using these peptides, generally as described in Examples 1 and 3 above. The results showed that vaccination with RTS.S caused the production of circulating activated T-cells which responded to several of the oligopeptides used in the assay, in all ten volunteers. These experiments demonstrated that high frequencies (up to 1/10,000 PBMC) of T-cells specific for certain peptides were induced by vaccination with RTS.S. The peptides that were most strongly recognised were those from the Th2 region and the conserved Region II of CSP suggesting that responses to those sequences of *P. falciparum* CSP may mediate protective immunity. Ongoing studies are applying the assay technique to study cellular immune responses induced by RTS.S in phase I/II infectious mosquito bite challenge studies and in field studies in Africa.

The invention claimed is:

1. An assay for identifying *Mycobacterium tuberculosis*-specific immediate effector T cells in a subject, comprising:
   (a) providing a sample from said subject containing T cells;
   (b) exposing said T cells to an immunogenic amount of a peptide subfragment of ESAT-6 that contains a CD8+ epitope; and
   (c) prior to the generation of new immediate effector T cells in the sample, determining whether said T cells are activated by said peptide subfragment by measuring secretion of a cytokine from said T cells;
wherein activation of said T cells identifies the presence of *Mycobacterium tuberculosis*-specific immediate effector T cells that were present in the original sample, in said subject.

2. The method of claim 1, wherein said T cells are peripheral blood mononuclear cells.

3. The method of claim 1, wherein the activation of said T cells is determined by measuring secretion of interferon-γ from said T cells.

4. The method of claim 1, wherein said subject is known to be suffering, or to have suffered from, infection with *Mycobacterium tuberculosis*.

5. The method of claim 4, wherein said infection is monitored.

6. An assay for identifying *Mycobacterium tuberculosis*-specific immediate effector T cells in a subject, comprising:
   (a) providing a sample from said subject containing T cells;
   (b) exposing said T cells to an immunogenic amount of a peptide subfragment of ESAT-6 that contains a CD8+ epitope;
   (c) incubating said T cells for a period of time which is not sufficient to effect differentiation of quiescent T cells to immediate effector T cells; and
   (d) determining whether said T cells are activated by said peptide subfragment by measuring secretion of a cytokine from said T cells,
wherein activation of said T cells identifies the presence of *Mycobacterium tuberculosis*-specific immediate effector T cells in said subject.

7. The method of claim 1 or 6, wherein said T cells are exposed to said peptide subfragment at 37° C.

8. The method of claim 6, wherein said incubation time is from 4 hours to 24 hours.

9. The method of claim 6, wherein said incubation time is from 6 hours to 16 hours.

* * * * *